United States Patent [19]
Golembeck et al.

[11] 4,140,008
[45] Feb. 20, 1979

[54] SYSTEM FOR TESTING FIRMNESS

[75] Inventors: Gerald A. Golembeck, Lake Elmo; Richard H. Eide, Minneapolis, both of Minn.

[73] Assignee: The United States Bedding Company, St. Paul, Minn.

[21] Appl. No.: 864,821

[22] Filed: Dec. 27, 1977

[51] Int. Cl.² ............................................. G01N 3/40
[52] U.S. Cl. ........................................ 73/78; 73/806; 73/161
[58] Field of Search ................... 73/161, 94, 90, 89, 73/78

[56] References Cited
U.S. PATENT DOCUMENTS

| | | | |
|---|---|---|---|
| 2,930,943 | 3/1960 | Ruge | 73/161 X |
| 3,195,347 | 7/1965 | Janapol | 73/161 X |
| 3,285,065 | 11/1966 | Ragen et al. | 73/161 |

*Primary Examiner*—Jerry W. Myracle
*Attorney, Agent, or Firm*—McDougall, Hersh & Scott

[57] ABSTRACT

A system for measuring or testing the firmness of a resilient object such as a mattress. A pressure applying platen or the like is driven by a motor into the object, and the pressure applied is measured through the utilization of a pressure sensitive transducer or the like. This generates electrical power proportional to the pressure, and a recorder displays information to provide a reading of the power generated. The generating means is also connected to control means for the motor, and a threshold circuit or the like is adapted to shut off and reverse the motor when the power generated reaches a predetermined level.

10 Claims, 5 Drawing Figures

SYSTEM FOR TESTING FIRMNESS

BACKGROUND OF THE INVENTION

This invention relates to a system for testing the firmness of mattresses and the like. The invention is particularly concerned with a tester capable of measuring the relative compression force necessary for deflecting springs, spring assemblies, foam samples, composites of foam and springs, and other resilient objects including completed cushions and mattresses.

Objects of the type referred to above are tested for various reasons. Testing is typically conducted on mattresses and similar objects for purposes of providing a firmness or comfort evaluation. The testing results also provide a means for quality control and evaluation of materials and products.

Forces applied during testing simulate the weight of individuals who would be likely to use such objects. Force measurements are useful for determining the ability of mattresses to remain reasonably flat or firm during use.

SUMMARY OF THE INVENTION

In accordance with this invention, a pressure applying means such as a platen is driven by a motor against the surface of a mattress or the like. A suitable pressure sensitive device is associated with the platen whereby electrical power is generated proportional to the pressure applied. A recorder is provided for displaying information including a reading of the power generated. This recorder is connected to the generating means so that the display of the recorder will provide a reading indicating the power generated. The recorder is preferably of the chart type with the chart being driven at a constant speed. By providing a constant speed motor for driving the platen, the information displayed on the chart will also include a reading of the degree of penetration of the platen relative to the mattress or other object being tested.

The information obtained in accordance with this invention may be employed for designating the grade of mattress produced. Thus, mattresses may be classified for sales purposes as "firm", "extra firm", "super firm", etc. The mechanism of this invention provides a display of information which will permit the categorizing of mattresses. It is important that the mechanism of this invention may be located along a production line whereby each mattress produced can be efficiently tested to achieve complete quality control and accuracy in advertising.

DETAILED DESCRIPTION OF THE DRAWINGS

The system of this invention will be described with reference to the testing of mattresses. As indicated, the mechanisms may be utilized for measuring or otherwise recording pressures and forces applied when deflecting springs, spring assemblies, foam samples, composites of foam and springs, and other resilient objects including completed cushions and mattresses. The invention is described with respect to mattresses particularly because the firmness of mattresses is of great importance to the manufacturer and user of the product.

Figure 2:
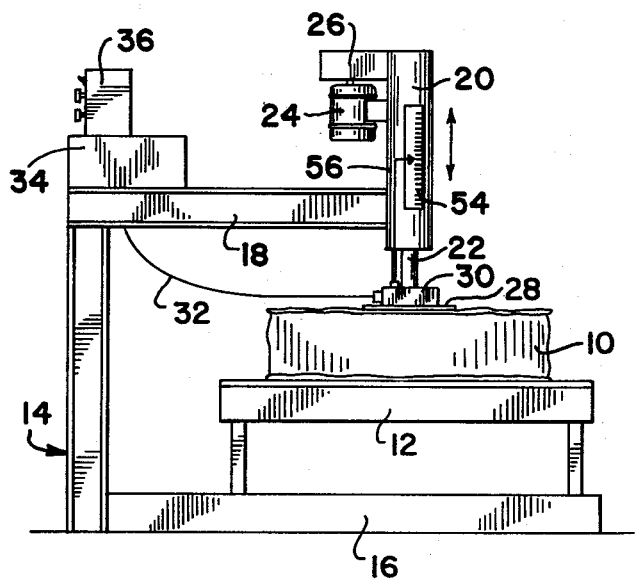
FIG. 2 is an elevational view of a mechanism characterized by the features of this invention; and, FIGS. 3, 4 and 5 comprise diagrammatic illustrations of recordings obtained utilizing the mechanisms of this invention.

FIG. 2 of the drawings illustrates a mattress 10 supported on platform 12. For purposes of this invention, it will be assumed that the platform 12 is located in a production line with any suitable conveyor means being employed for moving successive mattresses onto the platform. The invention is applicable to testing of mattresses under other circumstances, for example for the testing of mattresses taken from an existing inventory.

The testing system of this invention includes a supporting frame 14 having a bottom section 16 positioned on the floor and an overhanging section 18. The frame will preferably be made of strong structural materials so that the weight of elements of the system as well as the forces applied during testing will not bend the frame to the extent that readings would be affected.

The section 18 of the frame carries a cylinder 20 having a piston 22 movable therein. An electric motor 24 is supported on the cylinder, and gearbox 26 is interpositioned between the motor and cylinder. Various conventional means may be employed for driving the piston with a rack and pinion drive comprising an example.

The piston 22 supports a platen 28, and a pressure sensitive device 30 is supported on the platen. This device may comprise various pressure sensitive transducers, for example, a type utilizing piezoelectric means. Such means are provided so that electrical power will be generated in response to the mechanical forces to which the transducer is subjected.

Figure 1:
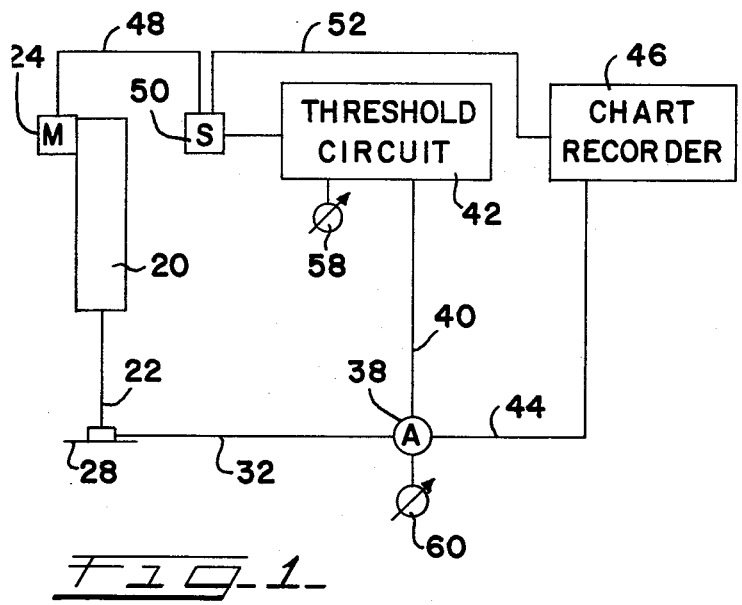
FIG. 1 is a schematic illustration of a circuit including elements of the type employed in the system of this invention.

A line 32 serves to connect the transducer to a recorder 34 and control box 36. As best shown in FIG. 1, the line 32 preferably extends to an amplifier 38 whereby an amplified signal will be transmitted through line 40 to threshold circuit device 42. This amplified signal is directed through line 44 to chart recorder 46. The drive motor 24 is connected through line 48 and switch means 50 to line 52 which in turn is connected to the chart recorder 46. When the switch means is in a condition such that the motor 24 is running in a direction to extend piston 22, the chart recorder 46 will also be running. Accordingly, the switch means provides the mechanism for moving the chart recorder in direct relationship with the extending movement of piston 22. Where an inking stylus or the like is engaged with the chart recorder, this will provide a direct indication on the chart recorder of the degree of extension of the piston. Similarly, where the platen on the end of the piston is penetrating a mattress, the degree of penetration will be readily observable by reference to the chart recorder.

The cylinder 20 may be provided with a scale 54 having needle 56 movable over the scale. As shown, this needle will move in accordance with the movement of the platen 28 so that an operator will have a visual indication of the degree of deflection while the recorder is operating. It will be appreciated that a digital display unit or the like could be readily connected to transducer 30 so that the operator would also have available a reading of the pressure applied throughout a testing operation.

The threshold circuit 42 may comprise any conventional device which will become conductive upon the application of sufficient voltage. Typically, an SCR would be provided in combination with a relay. When a predetermined voltage is achieved in response to the application of a certain magnitude of pressure, the relay would be operated whereby the switch means 50 would serve to halt the descending movement of the platen and to initiate reversing movement of the motor. In accordance with conventional practice, the threshold circuit will be provided with adjusting and calibrating means 58 so that a desired predetermined threshold position can be achieved. Adjusting means 60 for amplifier 38 is also provided, this means preferably being set so that zero load on the platen will correspond with zero voltage. One skilled in the art will readily recognize the steps necessary for calibrating and adjusting devices of the type described.

Figure 3:
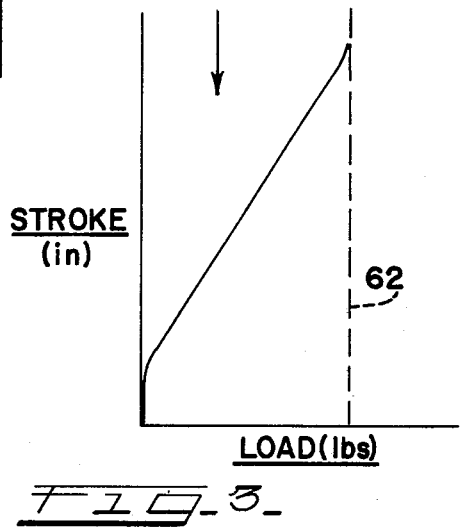
Figure 4:
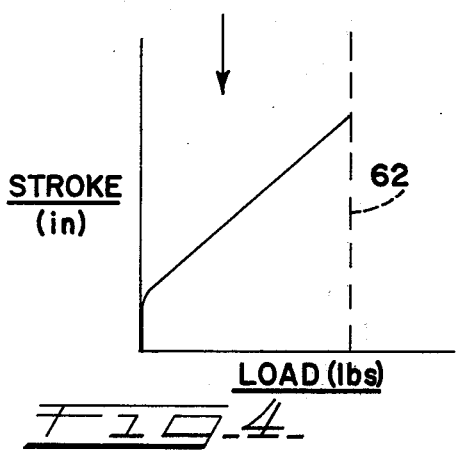
Figure 5:
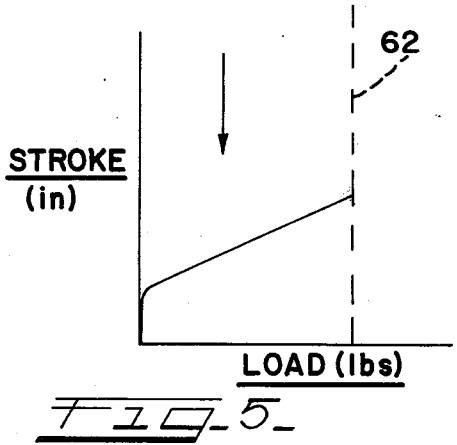

FIGS. 3, 4 and 5 illustrate typical chart recordings. In each instance, the "y" axis reading corresponds with the degree of deflection of a platen into a mattress or the like. The "x" axis provides a reading of the load applied at a given degree of deflection. Since the threshold circuit will always halt and reverse the platen movement when a given pressure level is achieved, the stylus markings of the respective charts all terminate along line 62. The number of inches of deflection necessary to achieve that pressure will vary directly in accordance with the firmness of a mattress. The mattress displaying the results of FIGS. 3, 4 and 5 may comprise "firm", "extra firm", and "super firm" mattresses, respectively.

A typical device in accordance with this invention will be capable of applying pressures to provide scale readings of between 200 and 300 pounds with 250 pounds being an example of a suitable setting for the threshold circuit operation. The drive motor for the system may be set to drive the platen between 1 and 30 inches per minute, 20 inches per minute being suitable for most applications with lower speeds in the order of 2 inches per minute being available for more sensitive testing.

A 1/6 horsepower reversible electric motor is suitable for operations utilizing a platen 12 inches in diameter. These and the above mentioned specifications will vary depending upon the specific application of the invention.

It will be understood that various changes and modifications may be made in the above described system which provide the characteristics of the invention without departing from the spirit thereof particularly as defined in the following claims.

That which is claimed is:

1. In a system for measuring the firmness of a resilient object wherein a pressure applying means is forced into the object and the pressure applied is measured, said pressure applying means being driven into the object by means of a motor, the improvement comprising pressure sensitive means associated with said pressure applying means, means for generating electrical power proportional to the pressure applied, a recorder for displaying information to provide a reading of the power generated, means connecting said generating means to said recorder, control means for said motor, and means connecting said generating means to said control means, said control means being adapted to terminate the driving movement of the pressure applying means into said object when the power generated reaches a predetermined level, said pressure applying means comprises a platen defining a pressure applying surface disposed in parallel relationship with a surface of said object, and wherein said motor comprises a reversible electric motor, a piston supporting said platen, a cylinder receiving said piston for reciprocal movement of the piston therein, said control means comprising switch means for reversing the direction of said motor and for starting and stopping the motor.

2. A system in accordance with claim 1 wherein the power generated by said generating means increases linearly relative to increases in pressure applied by said platen.

3. A system in accordance with claim 2 wherein said recorder comprises a chart recorder, the information on said recorder comprising a reading of the load applied along one axis and the degree of penetration into the object by the platen along the other axis.

4. A system in accordance with claim 3 wherein said means connected between said generating means and said control means comprises a threshold circuit device.

5. A system in accordance with claim 4 wherein said pressure sensitive means comprises a pressure sensitive transducer, and including an amplifier connected between said transducer and said threshold circuit device.

6. A system in accordance with claim 5 wherein the output of said amplifier is also connected to said chart recorder.

7. A system in accordance with claim 1 wherein said motor drives said platen at a rate between 1 and 30 inches per minute.

8. A system in accordance with claim 7 wherein said platen applies pressure of between 200 and 300 pounds per square inch.

9. A system in accordance with claim 1 including means for correlating the speed of said piston with the speed of said recorder whereby said recorder will automatically display the degree of penetration of said platen into said object.

10. A system in accordance with claim 9 wherein said platen is positioned adjacent the path of movement of mattresses in a production line whereby said platen is adapted to be applied to each mattress in the production line.

* * * * *